United States Patent
Yamada (10) Patent No.: US 11,890,531 B2
(45) Date of Patent: Feb. 6, 2024

(54) MAINTENANCE METHOD OF BOWLING BALL, PLASTICIZER

(71) Applicant: Yutaka Yamada, Tokyo (JP)

(72) Inventor: Yutaka Yamada, Tokyo (JP)

( * ) Notice: Subject to any disclaimer, the term of this patent is extended or adjusted under 35 U.S.C. 154(b) by 1024 days.

(21) Appl. No.: 16/536,288

(22) Filed: Aug. 8, 2019

(65) Prior Publication Data

US 2020/0054933 A1    Feb. 20, 2020

(30) Foreign Application Priority Data

Aug. 10, 2018 (JP) .................................. 2018-151373
Sep. 10, 2018 (JP) .................................. 2018-168556

(51) Int. Cl.
| | |
|---|---|
| *A63D 5/10* | (2006.01) |
| *C07C 67/00* | (2006.01) |
| *C11D 1/08* | (2006.01) |
| *A63B 37/00* | (2006.01) |
| *C07C 69/00* | (2006.01) |
| *C08K 5/10* | (2006.01) |

(52) U.S. Cl.
CPC ................ *A63D 5/10* (2013.01); *A63B 37/00* (2013.01); *C07C 67/00* (2013.01); *C07C 69/00* (2013.01); *C08K 5/10* (2013.01); *C11D 1/08* (2013.01)

(58) Field of Classification Search
CPC ................................... A63D 5/10; A63B 37/00
See application file for complete search history.

(56) References Cited

U.S. PATENT DOCUMENTS 6,407,201 B1 *   6/2002   Taylor .................... C08G 63/16
                                                          528/308
2015/0013731 A1   1/2015   Hardman et al.

FOREIGN PATENT DOCUMENTS

| JP | S59-22564 A | 2/1984 |
|---|---|---|
| JP | S59-022564 A | 2/1984 |
| JP | S64-2674 A | 1/1989 |
| JP | S64-002674 A | 1/1989 |
| JP | H02-28268 U | 2/1990 |
| JP | H2-028268 U | 2/1999 |
| JP | 2001-259082 A | 9/2001 |
| JP | 2001259082 A * | 9/2001 |

OTHER PUBLICATIONS

Machine translation of JP-2001259082-A.*
Japan Patent Office, Office Action for Japanese Patent Application No. 2019-145451, dated Nov. 5, 2019 (A machine translation is attached hereto).
Japan Patent Office, Office Action for Japanese Patent Application No. 2019-145451, dated Feb. 4, 2020 (A machine translation is attached hereto).

(Continued)

*Primary Examiner* — Deborah D Carr (57) ABSTRACT

The purpose of the present invention is to provide a maintenance method for restoring the flexibility of a surface layer of a bowling ball in which the flexibility of the surface layer is lost by volatilization or elution of a plasticizer. In order to solve the above-mentioned problems, a maintenance method of bowling ball is provided, characterized in that a plasticizer is applied to a surface layer of the bowling ball.

8 Claims, 1 Drawing Sheet

(56) References Cited

OTHER PUBLICATIONS

Drastic!, Renewal magic! Memo [online], instructions manual (usage instruction) and figures, amesmemo.blog113.fc2.com/blog-entry-1125.html, Feb. 14, 2020 ((Cited in Japanese Office Actions dated Feb. 4, 2020 and dated Jun. 16, 2020 for Japanese Patent Application No. 2019-145451 (Cite Nos. 2 and 4 of Non-Patent Literature Documents in this list)).
Japan Patent Office, Office Action for Japanese Patent Application No. 2019-145451, dated Jun. 16, 2020 (A machine translation is attached hereto).
Hellbent, Commercial supplies, Hellbent Equipment[online], Section "Hellbent Renewal Magic", https://web.archive.org/web/20150612095501/http://www.ark-wave.co.jp/contnt/hb/equip/equip.html, Jun. 12, 2015 (Cited in Japanese Office Action dated Jun. 16, 2020 for Japanese Patent Application No. 2019-145451(Cite No. 4 of Non-Patent Literature Documents in this list)).
Bowlers'Craft noshiro [online], Renewal Magic (Blue Label), https://web.archive.org/web/20150329214156/ https://www.noshiro-bowl.co.jp/index.php?main_page=product_info&cPath=112_174&products_id=9567, Mar. 29, 2015 (Cited in Japanese Office Action dated Jun. 16, 2020 for Japanese Patent Application No. 2019-145451(Cite No. 4 of Non-Patent Literature Documents in this list)).
Renewal Magic, Road to a bowling coach by Masaru Arimoto [Online], https://ameblo.jp/fourmilere/entry-11040752676.html, Oct. 8, 2011 (Cited in Japanese Office Action dated Jun. 16, 2020 for Japanese Patent Application No. 2019-145451(Cite No. 4 of Non-Patent Literature Documents in this list)).

* cited by examiner

MAINTENANCE METHOD OF BOWLING BALL, PLASTICIZER

CROSS REFERENCE TO RELATED APPLICATION

This application is a new U.S. patent application that claims benefit of Japanese Patent Application No. 2018-151373, filed on Aug. 10, 2018 and Japanese Patent Application No. 2018-168556 filed on Sep. 10, 2018. The entire contents of Japanese Patent Application Nos. 2018-151373 and 2018-168556 are hereby incorporated by reference.

TECHNICAL FIELD

The present invention relates to a maintenance method of bowling ball, plasticizer. In particular, it relates to a maintenance method of bowling ball by applying a plasticizer to a surface layer of the bowling ball. The invention further relates to a plasticizer for application to a surface layer of a bowling ball.

BACKGROUND

It is known that the bowling ball is formed of a core layer, an intermediate layer, a surface layer, or the like, and the surface layer is a layer made of a resin such as polyester or polyurethane (JP-U-2-28268). In addition, although the bowling ball contains a plasticizer or the like in a resin used for the surface layer to adjust the hardness and density, it is known that the plasticizer contained in the resin of the surface layer volatilizes in the air over time and elutes due to the influence of oil or the like applied to the lane.

It is known that bowling balls in which a plasticizer is volatilized or eluted from a surface layer lose flexibility of the surface layer and deteriorate its performance. For example, JP-A-64-2674 and JP-A-59-22564 disclose bowling balls having a surface layer which is difficult to absorb oil.

SUMMARY

However, even a bowling ball having a surface layer which is difficult to absorb oil cannot completely prevent absorption of oil, and elution of a plasticizer cannot be suppressed. Furthermore, it is fundamentally impossible to prevent the volatilization of the plasticizer in the air, and the problem arises that the flexibility of the surface layer of the bowling ball is lost over time.

It is therefore an object of the present invention to provide a maintenance method for restoring the flexibility of a surface layer of a bowling ball in which the flexibility of the surface layer is lost by volatilization or elution of a plasticizer.

As a result of intensive studies on the above problems, the present inventor has found that by applying a plasticizer to a bowling ball in which the plasticizer has volatilized or eluted, the flexibility of the surface layer of the bowling ball is restored to the same degree as that of an unused product, and has completed the present invention. That is, the present invention relates to the following maintenance method of bowling ball.

The maintenance method of bowling ball of the present invention for solving the above problems is characterized in that a plasticizer is applied to a surface layer of the bowling ball. According to the maintenance method of bowling ball of the present invention, by applying the plasticizer to the surface layer of the bowling ball in which the plasticizer is volatilized or eluted, the plasticizer is absorbed by the resin of the surface layer, and the flexibility of the surface layer of the bowling ball can be restored to a degree close to that of an unused product.

Next, in one embodiment of the method for maintaining a bowling ball of the present invention, the plasticizer is a compound having an oxyalkylene group. According to this feature, the plasticizer can efficiently penetrate to the deep layer portion of the surface layer of the bowling ball by the polarity of the oxyalkylene group, and the effect of the present invention can be further exhibited. In addition, by containing a plasticizer having polarity in the surface layer, absorption of oil can be suppressed.

Next, as one embodiment of the maintenance method of bowling ball of the present invention, the plasticizer is one or more compounds represented by the general formula (1) of (A).

(1)

[In the above formula, $R^1$ independently represents a hydrocarbon group having 1 to 10 carbon atoms, and $R^2$ independently represents a hydrocarbon group having 1 to 30 carbon atoms or a halogen atom, wherein the hydrocarbon group may contain a heteroatom, wherein n is a repeat number, represents an integer of 1 or more, and p represents an integer of 0 to 5, respectively.] According to this feature, since the plasticizer contains a compound having an ester structure, the plasticizer can interact with the resin used for the surface layer. Therefore, the effect that the plasticizer remaining in the surface layer or the applied plasticizer is less likely to volatilize or elute can be exhibited.

Next, as one embodiment of the maintenance method of bowling ball of the present invention, the plasticizer is one or more compounds represented by the general formula (2) of (B).

(2)

[In the above formula, $R^3$ represents a hydrocarbon group having 1 to 20 carbon atoms, wherein the hydrocarbon group may contain a heteroatom, $R^4$ independently represents a hydrocarbon group having 1 to 30 carbon atoms or a halogen atom, wherein the hydrocarbon group may contain a heteroatom, and m represents an integer of 0 to 5.]

According to this feature, since the plasticizer contains a compound having an ester structure, the effect that the plasticizer remaining in the surface layer or the applied plasticizer is less likely to volatilize or elute can be exhibited.

Next, as one embodiment of the maintenance method of bowling ball of the present invention, the plasticizer is one or more compounds represented by the general formula (3):

(3)

[In the above formula, $R^5$, $R^6$ independently represents a hydrogen atom or a hydrocarbon group having 1 to 20 carbon atoms, wherein the hydrocarbon group may contain a heteroatom.] According to this feature, since the plasticizer contains the compound having the above structure, the effect that the plasticizer remaining in the surface layer or the applied plasticizer is less likely to volatilize or elute can be exhibited.

Next, as one embodiment of the maintenance method of bowling ball of the present invention, the surface layer of the bowling ball is one or more resins selected from ebonite, polyester, polyethylene, polypropylene, polycarbonate, polyamide, polyurethane, polyimide, acrylic resin, polylactic acid, polyvinyl chloride, polybutadiene, polyisoprene, and epoxy resin.

According to this feature, since it is possible to cope with a bowling ball having a surface layer containing various resins, it is possible to apply it to a bowling ball made of a wide range of materials.

Next, as one embodiment of the maintenance method of bowling ball of the present invention, the bowling ball is characterized in that the bowling ball has been subjected to an oil removal treatment.

According to this feature, since the plasticizer is applied to the bowling ball subjected to the oil removal treatment, the plasticizer can efficiently penetrate to the deep layer portion of the surface layer portion. Further, since the plasticizer is infiltrated into the portion of the surface layer where the oil has been absorbed, it is possible to suppress reabsorption of the oil.

Next, an embodiment of the maintenance method of bowling ball of the present invention includes the following steps.

[Step 1]: Preparing bowling balls
[Step 2]: applying a plasticizer to the surface layer of the bowling ball prepared in Step 1

According to this feature, by applying the plasticizer to the surface layer of the bowling ball in which the plasticizer has volatilized or eluted, the plasticizer is absorbed by the resin of the surface layer, and the flexibility of the surface layer of the bowling ball can be restored to a degree close to that of an unused product.

Next, one embodiment of the maintenance method of bowling ball of the present invention further includes any or both of the following steps.

[Step 3]: Sealing the bowling ball applied with the plasticizer in Step 2
[Step 4]: Holding the bowling ball for a fixed time while adjusting the temperature of the bowling ball According to this feature, the plasticizer can be more efficiently absorbed into the resin in the surface layer of the bowling ball, and the flexibility of the surface layer of the bowling ball can be restored to a degree closer to the unused product.

The plasticizer of the present invention for solving the above-mentioned problems is characterized in that it is used for application to a surface layer of a bowling ball.

By applying the plasticizer to the surface layer of the bowling ball, the flexibility of the surface layer of the bowling ball, which has become hard due to volatilization or elution of the plasticizer, can be restored to a degree close to that of the unused product.

According to the present invention, it is possible to provide a maintenance method for restoring the flexibility of a surface layer of a bowling ball in which the flexibility of the surface layer is lost by volatilization or elution of a plasticizer.

BRIEF DESCRIPTION OF THE DRAWINGS

Other features and advantages of the claimed invention will be apparent from the ensuing description, taken in conjunction with the accompanying drawings, in which:

DESCRIPTION

Next, the best mode for carrying out the present invention will be explained.

[Maintenance Method of Bowling Ball]

The maintenance method of bowling ball of the present invention is characterized in that a plasticizer is applied to a surface layer of the bowling ball.

<Bowling>

Bowling is one of the sporting events held indoors, in which 10 targets called pins are arranged in a regular triangle facing the top in front of the lane, and the player rolls the ball (bowling ball) toward pins and competes the total number of pins knocked down.

<Bowling-Ball>

The bowling ball is a spherical object having a diameter of about 21.8 cm and a weight of 1.81 kg to 7.25 kg, and a surface layer portion made of resin. The hardness of the bowling ball is measured by a hardness meter (REX DUROMETER, TYPE D, Model:1700, manufactured by REX GAUGE Corporation) of Durometer D in an environment of 25 degrees Celsius, and it is defined that the hardness of the bowling ball is 72 degrees or more.

The surface layer of the bowling ball is preferably a hard rubber such as ebonite, a polyester such as polyethylene terephthalate or polyethylene naphthalate, a polyethylene, a polypropylene, a polycarbonate, a polyamide, a polyurethane, a polyimide, an acrylic resin, a rubber component such as polylactic acid or polyvinyl chloride, a rubber component such as polybutadiene or polyisoprene, and one or more resins such as an epoxy resin, and in particular, a resin made of polyester or polyurethane is preferable. The surface layer of the bowling ball may include a glass balloon, a whisker, or the like.

Further, as the bowling ball used in the maintenance method of the bowling ball of the present invention, it is preferable to use a ball whose surface is cleaned with a towel composed of a microfiber or a ball subjected to an oil removal treatment. The oil removal treatment is a treatment of removing oil from a bowling ball in a state where the oil on the lane is absorbed. The method of the oil removal treatment is not particularly limited, and a general method can be used. For example, a method of applying heat to a bowling ball, a method of immersing the bowling ball in hot water, or the like is preferable, and if a surfactant such as a detergent is added to the hot water, the oil can be more effectively extracted. In addition, a plasticizer can be applied to the bowling ball in a warmed state after the oil removal process.

<Plasticizer>

The plasticizer used in the maintenance method of bowling ball of the present invention is not particularly limited, and is applied to a resin and penetrated to restore the flexibility of the surface layer of the bowling ball. The chemical structure of the plasticizer in the present invention is preferably an organic compound having a polar structure. Examples of the polar structure include an amino group, an oxa group, a carbonyl group, an oxycarbonyl group, a carbonyloxy group, an epoxy group, a mercapto group, and a thia group. Since the plasticizer has a polar structure, the surface resin can be infiltrated by compatibility of the surface layer of the bowling ball with a polar group such as a resin. Further, as the chemical structure of the plasticizer in the present invention, it is preferable to have a nonpolar structure. Examples of the nonpolar structure include an aromatic ring such as a benzene ring or a naphthalene ring, an alkyl group such as a methyl group or an ethyl group. Since the plasticizer has a non-polar structure, the surface resin can be infiltrated by compatibility of the surface layer of the bowling ball with a non-polar group such as a resin. As the plasticizer, one type alone can be used, but a mixture or a composition in which two or more types are combined is also included in the plasticizer.

When two or more types of plasticizers are included in the plasticizer in the maintenance method of the present invention, the content is appropriately adjusted according to the type of resin used for the bowling ball surface layer. By adjusting the type of the plasticizer, it is possible to impart an effect of penetrating into the bowling ball surface layer, an effect of increasing the holding force of the applied plasticizer, and an effect of hardly volatilizing or eluting, and the like.

Specific examples of plasticizers include aromatic carboxylic acid ester compounds [phthalate esters(2-ethylhexyl phthalate, methyl phthalate, ethyl phthalate, butyl phthalate, isononyl phthalate, isodecyl phthalate, undecyl phthalate, butyl benzyl terephthalate, etc.), terephthalate esters (methyl terephthalate, ethyl terephthalate, butyl phthalate, 2-ethylhexyl terephthalate, isononyl terephthalate, isodecyl terephthalate, undecyl terephthalate, butyl benzyl terephthalate, etc.)], aliphatic monocarboxylic acid compounds[Methylacetylricinoleate, etc.], aliphatic dicarboxylic acid compounds[Dibutyladipate, Diisobutyladipate, di(2-ethylhexyl) adipate, diisononyl adipate, bis[2-(2-butoxyethoxy)ethyl] adipate, bis(2-ethylhexyl)azelate, dibutylcebacate, Bis(2-ethylhexyl) cebacate, diethylsuccinate, etc.], tricarboxylic acid ester compounds [tris(2-ethylhexyl) trimellitate, trimellitic acid isononyl ester, trimellitic acid mixed alkyl ester, dipentaerythritol ester, citrate esters (triethyl citrate, tributyl citrate)], tetracarboxylic acid ester compounds [pyromerite 2-ethylhexyl, pyromethylphosphate mixed straight chain alkyl ester, Phosphate esters[triphenylphosphate, Tricresylphosphates, trixylethylphosphates, crephenyl phosphates, 2-ethylhexyldiphenyl phosphate, etc.], lysilenolic acid ester [methyl acetyllysilenol, etc.], polyester (adipic acid-propylene glycol polyester with a molecular weight of about 800 to 2200), adipic acid-1,3-butylene glycol polyesters (molecular weight of about 800 to 2200); phthalic acid polyesters (molecular weight of about 650); dibasic acids such as adipic acid, sebatic acid, and phthalic acid; polymers of glycolic acids such as 1,2-propanediol, butanediol, etc.; acetic acid esters [glyceryl triacetate, etc.]; sulfonamides [N-butylbenzenesulfonamide, etc.]; epoxy compounds [epoxy-anine oil, epoxy fatty acid octyl esters, epoxy fatty acid alkyl esters]; benzoic acid esters of benzoic acid esters [diethylene glycol diglycol, dipropylenediglycol, dipropylenediglycol, etc.), and the like.

In the maintenance method of the present invention, preferable plasticizers are, for example, (A) a benzoic acid ester compound, (B) an aromatic carboxylic acid ester compound, and (C) citric acid esters.

(A) Examples of the benzoic acid ester compound include compounds having an oxyalkylene group represented by the following general formula (1).

Although $R^1$ in the formula (1) independently represents "a hydrocarbon group having 1 to 10 carbon atoms", the "hydrocarbon group" may have each of a straight chain structure, a branched structure, and a cyclic structure, and may be any of a saturated hydrocarbon group, an aromatic hydrocarbon group, and the like.

In the general formula (1), the number of carbon atoms of the $R^1$ hydrocarbon group is preferably 1 to 10. The lower limit of the number of carbon atoms of $R^1$ is preferably 2 or more, more preferably 3 or more. The upper limit value is preferably 8 or less, more preferably 6 or less, and particularly preferably 4 or less. When the $R^1$ is an aromatic hydrocarbon group, the number of carbon atoms is usually 6 or more. By setting the number of carbon atoms of the hydrocarbon group of the $R^1$ in the above ranges, the permeability to the surface layer of the bowling ball can be improved.

Examples of the $R^1$ include a methylene group ($-CH_2-$), an ethylene group ($-C_2H_4-$), an n-propylene group ($-nC_3H_6-$), an i-propylene group ($-iC_3H_6-$), an n-butylene group ($-nC_4H_8-$), an n-pentylene group ($-nC_5H_{10}-$), an n-hexylene group ($-nC_6H_{12}-$), a cyclohexylene group, a phenylene group ($-C_6H_4-$), and the like, and preferably, an ethylene group, an n-propylene group, and an i-propylene group.

In the formula (1), "n" represents the number of repeating units of ($-R^1-O-$) units, and preferably represents an integer of 1 or more. The lower limit value is preferably 2 or more, more preferably 3 or more. The upper limit is preferably 100 or less, more preferably 50 or less, still more preferably 30 or less, and particularly preferably 20 or less. By setting "n" within the above range, the plasticizer can efficiently penetrate to the deep portion of the surface layer of the bowling ball.

In the formula (1), $R^2$ independently represents a hydrocarbon group having 1 to 30 carbon atoms or a halogen atom, wherein the hydrocarbon group may contain a heteroatom, but "a hydrocarbon group" may have each of a straight chain structure, a branched structure, a cyclic structure, and a carbon-carbon unsaturated bond (carbon-carbon double bond, carbon-carbon triple bond), and may be any of a saturated hydrocarbon group, an unsaturated hydrocarbon group, an aromatic hydrocarbon group, and the like. The term "may contain a heteroatom" means that a hydrogen atom of a hydrocarbon group may be substituted with a heteroatom, i.e., a monovalent functional group containing a nitrogen atom, an oxygen atom, a sulfur atom, a halogen atom, or the like, or that a carbon atom within a carbon skeleton of a hydrocarbon group may be substituted with a divalent or more functional group (linking group) containing a nitrogen atom, an oxygen atom, a sulfur atom, a halogen atom, or the like.

In the formula (1), the number of carbon atoms of the $R^2$ hydrocarbon group is preferably 1 to 30. The lower limit of the number of carbon atoms of $R^2$ is preferably 4 or more, more preferably 6 or more. The upper limit is preferably 20 or less, more preferably 10 or less, and particularly preferably 8 or less. When the $R^2$ is an aromatic hydrocarbon group, the number of carbon atoms is usually 6 or more. If the number of carbon atoms of the hydrocarbon group of the $R^2$ is larger than 30, the permeability to the article is deteriorated, and the plasticizing action cannot be sufficiently exerted.

Functional groups and linking groups included in the $R^2$ include an amino group (—N<), an isocyanate group (—NCO), an oxa group (—O—), a carbonyl group (—C(=O)—), an oxycarbonyl group (—OC(=O)—), a carbonyloxy group (—C(=O)O—), an epoxy group, a mercapto group (thiol group, —SH), a thia group (—S—), a fluoro group (fluorine atom, —F), a chloro group (chloro atom, —Cl), a bromo group (bromine atom, —Br), an iodo group (iodo atom, —I), and the like.

Examples of the $R^2$ include a methyl group (—CH$_3$, -Me), an ethyl group (—C$_2$H$_5$, -Et), an n-propyl group (-nC$_3$H$_7$, -$^n$Pr), an i-propyl group (-iC$_3$H$_7$, -$^i$Pr), an n-butyl group (-nC$_4$H$_9$, -$^n$Bu), a t-butyl group (-t C$_4$H$_9$, -$^t$Bu), an n-pentyl group (-nCH$_{11}$), an n-hexyl group (-n C$_6$H$_{13}$, -$^n$Hex), a cyclohexyl group (-c C$_6$H$_{11}$, —Cy), an ethylhexyl group, an allyl group (—CH=CH—CH2), a vinyl group (—CH=CH$_2$), a phenyl group (—C$_6$H$_5$, -Ph), a benzyl group (—CH$_2$—C$_6$H$_5$, —Bn), a hydrocarbon group such as biphenyl group, naphthyl group, a hydrocarbon group, a halogen atoms such as fluoro group, chloro group, bromo group, and iodo group, and the like.

In the formula (1), "p" corresponds to the number of substituents "$R^2$" substituted for the benzene ring, and each is an integer of 0 to 5. The lower limit value is preferably 1 or more, more preferably 2 or more. The upper limit value is preferably 4 or less, more preferably 3 or less.

(A) Specific examples of the component include compounds represented by any of the following formula (1-1) to (1-10), for example.

(1-1)

(1-2)

(1-3)

(1-4)

(1-5)

(1-6)

(1-7)

(1-8)

(1-9)

(1-10)

(A) Components can be prepared, for example, by transesterifying benzoic acid with diol compounds such as ethylene glycol, propylene glycol (1,2-propanediol), and 1,3-propanediol. Commercially available products include benzoic acid glycol ester (JP120: J-PLUS Co., Ltd.), and the like.

(B) Examples of the aromatic carboxylic acid ester compound include compounds represented by the following general formula (2).

(2)

In the formula (2), $R^3$ represents "a hydrocarbon group having 1 to 20 carbon atoms, wherein the hydrocarbon group may contain a heteroatom", but "may contain a heteroatom" and "hydrocarbon group" are synonymous with those described above.

In the formula (2), the number of carbon atoms of the $R^3$ hydrocarbon group is preferably 1 to 20. The lower limit of the number of carbon atoms of $R^3$ is preferably 4 or more, more preferably 6 or more. The upper limit value is preferably 15 or less, more preferably 10 or less, and particularly preferably 8 or less. When the $R^3$ is an aromatic hydrocarbon group, the number of carbon atoms is usually 6 or more. By setting the number of carbon atoms of the hydrocarbon group of the $R^3$ in the above ranges, the permeability to the surface layer of the bowling ball can be improved.

Functional groups and linking groups included in the $R^3$ include an amino group (—N<), an isocyanate group (—NCO), an oxa group (—O—), a carbonyl group (—C(=O)—), an oxycarbonyl group (—OC(=O)—), a carbonyloxy group (—C(=O)O—), an epoxy group, a mercapto group (thiol group, —SH), a thia group (—S—), a fluoro group, a chloro group, a bromo group, and an iodo group.

Examples of the $R^3$ include, a methyl group (—CH$_3$, -Me), an ethyl group (—C$_2$H$_5$, -Et), an n-propyl group (-nC$_3$H$_7$, -$^n$Pr), an i-propyl group (-iC$_3$H$_7$, -$^i$Pr), an n-butyl group (-nC$_4$H$_9$, -$^n$Bu), a t-butyl group (-tC$_4$H$_9$, -$^t$Bu), an n-pentyl group (-nC$_5$H$_{11}$), an n-hexyl group (-nC$_6$H$_{11}$), a cyclohexyl group (-cC$_6$H$_{11}$, —Cy), an ethylhexyl group, an allyl group (—CH=CH—CH$_2$), a vinyl group (—CH=CH$_2$), a phenyl group (—C$_6$H$_5$, -Ph), a benzyl group (—CH$_2$—C$_6$H$_5$, -Bn), a biphenyl group, a naphthyl group, a 3-glycidoxy group, a 3-propyl group, and a 3-propyl group, N-2-(aminoethyl)-3-aminopropyl groups, and the like.

In the formula (2), $R^4$ independently represents" a hydrocarbon group having 1 to 30 carbon atoms, wherein the hydrocarbon group may contain a heteroatom, but "a hydrocarbon group having 1 to 30 carbon atoms which may contain a heteroatom" has the same meaning as described above.

In the formula (2), the number of carbon atoms of the $R^4$ hydrocarbon group is preferably 1 to 30. The lower limit of the number of carbon atoms of $R^4$ is preferably 4 or more, more preferably 6 or more. The upper limit is preferably 20 or less, more preferably 10 or less, and particularly preferably 8 or less. When the $R^4$ is an aromatic hydrocarbon group, the number of carbon atoms is usually 6 or more. If the number of carbon atoms of the hydrocarbon group of the $R^4$ is larger than 30, the permeability to the article is deteriorated, and the plasticizing action cannot be sufficiently exerted.

Functional groups and linking groups included in the $R^4$ include an amino group (—N<), an isocyanate group (—NCO), an oxa group (—O—), a carbonyl group (—C(=O)—), an oxycarbonyl group (—OC(=O)—), a carbonyloxy group (—C(=O)O—), an epoxy group, a mercapto group (thiol group, —SH), a thia group (—S—), a fluoro group, a chloro group, a bromo group, and an iodo group.

Example of $R^4$ include, a methyl group (—CH$_3$, -Me), an ethyl group (—C$_2$H$_5$, -Et), an n-propyl group (-nC$_3$H$_7$, -$^n$Pr), an i-propyl group (-iC$_3$H$_7$, -$^i$Pr), an n-butyl group (-nC$_4$H$_9$, -$^n$Bu), a t-butyl group (-t C$_4$H$_9$, -$^t$Bu), an n-pentyl group (-nC$_5$H$_{11}$), an n-hexyl group (-nC6H13), a cyclohexyl group (-cC$_6$H$_{11}$, —Cy), an ethylhexyl group, an allyl group (—CH=CH—CH$_2$), a vinyl group (—CH=CH$_2$), a phenyl group (—C$_2$H$_5$, -Ph), a benzyl group (—CH$_2$—C$_6$H$_5$, -Bn), a biphenyl group, a naphthyl group, a 3-glycidoxypropyl group, a 3-(Methacryloxy)propyl group, a 3-(Acryloxy)propyl group, a N-2-(aminoethyl)-3-aminopropyl group, carbonyloxymethyl, carbonyloxyethyl, carbonylmethylpropyl, carbonyloxybutyl, carbonyloxyhexyl, carbonyloxyoctyl, carbonyloxy-2-ethylhexyl group, carbonyloxyphenyl group, carbonyloxybenzyl group, halogen atoms such as fluoro group, chloro group, bromo group, and iodo group, and the like.

In the formula (2), "m" corresponds to the number of substituents "$R^4$" substituted for the benzene ring, and is an integer of 0 to 5. The lower limit value is preferably 1 or more, more preferably 2 or more. The upper limit value is preferably 4 or less, more preferably 3 or less.

(B) The compound represented by the component may be a compound represented by the following formula (2-1), and specific examples thereof include compounds represented by any of the following formula (2-2) to (2-11), for example.

(2-1)

(2-2)

(2-3)

(2-4)

(2-5)

(2-6)

(2-7)

(2-8)

(2-9)

(2-10)

(2-11)

(B) The component can be produced, for example, by transesterifying an aromatic carboxylic acid such as phthalic acid with an alcohol such as 2-ethylhexanol. Commercially available products include bis(2-ethylhexyl) phthalate (DOP: J-PLUS Co., Ltd.), dibutyl phthalate (DBP), butyl benzyl phthalate (BBP), and the like.

(C) Examples of the citric acid esters include compounds represented by the following general formula (3).

(3)

In the formula (3), $R^5$, $R^6$ independently represents a hydrogen atom, "a hydrocarbon group having 1 to 20 carbon atoms, wherein the hydrocarbon group may contain a heteroatom, but "a heteroatom" and "a hydrocarbon group" are synonymous with those described above.

In the formula (3), the number of carbon atoms of the $R^5$, $R^6$ hydrocarbon group is preferably 1 to 20. The lower limit of the number of carbon atoms of the $R^5$, $R^6$ is preferably 1 or more, more preferably 2 or more. The upper limit value is preferably 10 or less, more preferably 6 or less, and particularly preferably 4 or less. When the $R^5$, $R^6$ is an aromatic hydrocarbon group, the number of carbon atoms is usually 6 or more. If the number of carbon atoms of the hydrocarbon group of the $R^5$, $R^6$ is larger than 20, the permeability to the article is deteriorated, and the plasticizing action cannot be sufficiently exerted.

Functional groups and linking groups included in the $R^5$, $R^6$ include an amino group (—N<), an isocyanate group (—NCO), an oxa group (—O—), a carbonyl group (—C(=O)—), an oxycarbonyl group (—OC(=O)—), a carbonyloxy group (—C(=O)O—), an epoxy group, a mercapto group (thiol group, —SH), a thia group (—S—), a fluoro group, a chloro group, a bromo group, and an iodo group.

Example of $R^5$, $R^6$ include, a methyl group (—$CH_3$, -Me), an ethyl group (—$C_2H_5$, -Et), an n-propyl group (-$nC_3H_7$, -$^n$Pr), an i-propyl group (-$iC_3H_7$, -$^i$Pr), an n-butyl group (-$nC_4H_9$, -$^n$Bu), a t-butyl group (-$tC_4H_9$, -$^t$Bu), an n-pentyl group (-$nC_5H_{11}$), an n-hexyl group (-$nC_6H_{13}$), a cyclohexyl group (-$cC_6H_{11}$, —Cy), an ethylhexyl group, an allyl group (—CH=CH—$CH_2$), a vinyl group (—CH=$CH_2$), a phenyl group (—$C_2H_5$, -Ph), a benzyl group (—$CH_2$—$C_6H_5$, -Bn), an acetyl group, an acetylbiphenyl group, a methacrylic group, a 3-propyl group, a 3-propyl group, and a 3-propyl group Examples include N-2-(aminoethyl)-3-aminopropyl groups, preferably $R^5$, is an acetyl group and $R^6$ is an n-butyl group.

(C) Specific examples of the component include, for example, a compound represented by the following formula (3-1).

(3-1)

(C) The components can be prepared, for example, by transesterifying citric acid. Commercially available products include tributyl acetyl citrate (ATBC: J-PLUS Co., Ltd.), and the like.

For the plasticizer in the maintenance method of the present invention, the lower limit value of the content of the component (A) is, for example, 5% or more, 10% or more, 20% or more, 30% or more, 40% or more, 50% or more, 60% or more, 70% or more, 80% or more, 90% or more, 95% or more, and the upper limit value is, for example, 95% or less, 90% or less, 80% or less, 70% or less, 70% or less, 60% or less, 50% or less, 40% or less, 30% or less, 20% or less, 10% or less, 5% or less. With respect to the plasticizer in the maintenance method of the present invention, since the component (A) can interact with the resin used for the surface layer, the plasticizer can penetrate more into the bowling ball surface layer. For the plasticizer in the maintenance method of the present invention, the lower limit value of the content of the component (B) is, for example, 5% or more, 10% or more, 20% or more, 30% or more, 40% or more, 50% or more, 60% or more, 70% or more, 80% or more, 90% or more, 95% or more, and the upper limit value is, for example, 95% or less, 90% or less, 80% or less, 70% or less, 70% or less, 60% or less, 50% or less, 40% or less, 30% or less, 20% or less, 10% or less, 5% or less. By containing the component (B) in the plasticizer in the maintenance method of the present invention, the effect that the plasticizer remaining in the surface layer or the applied plasticizer is less likely to volatilize or elute can be exhibited. For the plasticizer in the maintenance method of the present invention, the lower limit value of the content of the component (C) is, for example, 5% or more, 10% or more, 20% or more, 30% or more, 40% or more, 50% or more, 60% or more, 70% or more, 80% or more, 90% or more, 95% or more, and the upper limit value is, for example, 95% or less, 90% or less, 80% or less, 70% or less, 70% or less, 60% or less, 50% or less, 40% or less, 30% or less, 20% or less, 10% or less, 5% or less. By containing the component (C) in the plasticizer in the maintenance method of the present invention, it is possible to exert the effect that the plasticizer remaining in the surface layer or the applied plasticizer is harder to volatilize or elute.

The plasticizer used in the maintenance method of bowling ball of the present invention preferably contains 80 to 99.99% by mass of the component (A) and 0.01 to 20% by mass of the component (B) or the component (C), for example, when the components (A) and (B) are mixed and used, or when the components (A) and (C) are mixed and used. (A) The lower limit value of the component is preferably 85% by mass or more, more preferably 90% by mass or more. The upper limit is preferably 99% by mass or less, more preferably 96% by mass or less, more preferably 94% by mass or less, and particularly preferably 92% by mass or less. (B) The lower limit value of the component or the component (C) is preferably 1% by mass or more, more preferably 4% by mass or more, and still more preferably 6% by mass or more. The upper limit is preferably 15% by mass or less, more preferably 10% by mass or less. By setting the content of the plasticizer in the above range, the plasticizer can penetrate further into the bowling ball surface layer, and further, elution of the plasticizer from the surface layer can be suppressed.

To the plasticizer used in the maintenance method of bowling ball of the present invention, known additives such as an antioxidant, an ultraviolet absorber, a flame retardant, an antistatic agent, a pigment, a dye, and a filler can be added in addition to the plasticizer such as the above-mentioned components (A), (B), and (C) to the extent that the characteristics are not impaired.

Antioxidants include thioether compounds (such as dilauryl 3,3'-thiodipropionate (DLTDP)), phenolic compounds (such as 2,6-di-t-butyl-p-cresol (BHT), butylated hydroxyanisole (BHA)), amine compounds (such as octylated diphenylamine), phosphorus compounds (such as triphenylphosphite (TPP)), and the like. Examples of the ultraviolet absorber include salicylic acid-based compounds [phenylsalicylate, etc.], acrylate-based compounds [2-ethylhexyl-2-cyano-3,3'-diphenylacrylate, etc.], benzotriazole-based compounds [2-(2'-hydroxy-5'-methylphenyl)benzotriazole, etc.], and benzophenone-based compounds [2-hydroxy-4-methoxybenzophenone, etc.].

Examples of the flame retardant include brominated compounds (pentabromodiphenyl ether, octabromodiphenyl ether, decabromodiphenyl ether, tetrabromobisphenol A, hexabromobenzene, and the like), chlorinated compounds (chlorinated paraffin and the like), phosphate triester compounds (triphenylphosphate and the like), and inorganic compounds (antimony trioxide, magnesium hydroxide, borate, zinc borate, barium metaborate, aluminum hydroxide, red phosphorus, magnesium hydroxide, ammonium polyphosphate and the like).

Examples of antistatic agents include ionic antistatic agents [anionic surfactants [sulfonate type (aliphatic sulfonate, etc.)), sulfuric acid ester type (higher alcohol sulfate salt, higher alcohol ethylene oxide adduct sulfate salt, etc.), phosphate ester type (higher alcohol ethylene oxide adduct phosphate ester salt, etc.), cationic surfactants [quaternary ammonium salt type, etc.], amphoteric surfactants [betaine type surfactants, etc.], nonionic antistatic agents [nonionic surfactants [polyethylene glycol type (higher alcohol ethylene oxide adduct, polyethylene glycol fatty acid ester, etc.)], polyhydric acid esters [polyether esters, etc.], polyhydric acid esters [polyether esters, etc.]. Examples of the pigment include inorganic pigments (bengala, titanium oxide, chelating azo, yellow lead, cadmium pigment, group blue, etc.), and organic pigments (azochelate, monoazo, disazo, condensed disazo, bendiimidazoline, phthalocyanine, quinacridone, dioxazine, isoindolinone, thioindigo, perylene, anthraquinone, quinophthalone, etc.). Examples of the dye include anthraquinone indigo, azo, sulfide, triphenylmethane, pyrazolone, stilbene, alizarin, diphenylmethane, xanthene, acridine, quinone imine, thiazole, methine, nitro, nitroso, aniline, and the like.

Examples of the filler include calcium carbonate, clay, talc, silicic acid, silicate, asbestos, mica, glass fibers, carbon fibers, metal (such as aluminum) fibers, glass balloons, ceramic whiskers, titanium whiskers, and the like.

The plasticizer used in the maintenance method of bowling ball of the present invention may be solvent-free, but may contain an organic solvent or the like. The organic solvent is not particularly limited, but a solvent capable of dissolving a plasticizer such as the above-mentioned components (A), (B), and (C) is preferable. Examples of the organic solvent include a halogenated hydrocarbon solvent such as methylene chloride or chloroform, an ester solvent such as ethyl acetate, propyl acetate or butyl acetate, a ketone solvent such as acetone, methyl ethyl ketone, diethyl ketone, methyl isobutyl ketone or cyclohexanone, and an aromatic solvent such as toluene or xylene.

Furthermore, the plasticizer of the present invention is characterized in that it is used for application to a surface layer of a bowling ball. By applying the plasticizer to the surface layer of the bowling ball, the surface layer of the bowling ball which has been volatilized or eluted and has lost its flexibility can be restored to a degree close to that of the unused product. The plasticizer is not particularly limited, and any plasticizer may be used as long as it is applied to the surface layer of the bowling ball to restore the flexibility of the surface layer of the bowling ball.

<Method of Applying Plasticizer>

The maintenance method of bowling ball of the present invention preferably includes the following steps. Steps 3 and 4 preferably include either or both steps.

[Step 1]: Preparing bowling balls

[Step 2]: applying a plasticizer to the surface layer of the bowling ball prepared in Step 1

[Step 3]: Sealing the bowling ball applied with the plasticizer in Step 2

[Step 4]: Holding the bowling ball for a fixed time while adjusting the temperature of the bowling ball As the bowling ball in the step 1, as a pretreatment, an operation of heating the bowling ball to remove oil permeated into the ball, or an operation of removing dust such as dust on the surface of the bowling ball using a brush, a towel, or the like may be performed. Examples of the heating method include a method of heating with a heater, a dryer, or the like, and a method of immersing in hot water. As a method of the oil removal treatment, a method of immersing a bowling ball in hot water or the like is preferable, and if a surfactant such as a neutral detergent is added to the hot water, the oil can be more effectively removed. By using a ball from which dust or the like has been removed or a ball from which oil has been removed, the plasticizer can be efficiently infiltrated into the surface layer of the bowling ball.

The temperature to which heat is applied and the temperature of the hot water are not particularly limited, and are preferably, for example, 40° C. to 90° C. The lower limit value is preferably 50° C. or more, more preferably 60° C. or more. The upper limit is preferably 80° C. or less, more preferably 70° C. By setting the temperature to which heat is applied or the temperature of the hot water to 40° C. to 90° C., the oil in the bowling bowl can be efficiently extracted.

The method of applying the plasticizer to the surface layer of the bowling ball in Step 2 is not particularly limited, and may be any method as long as it can be applied over the entire surface of the bowling ball. For example, a method of placing a bowling ball in a bag or the like and dropping the bowling ball directly, a method of applying the bowling ball directly with a brush, a brush, a gauze, a applying container, or the like, and a method of dipping the bowling ball into a container storing a plasticizer can be given. By applying by the above-described method, the plasticizer can be efficiently infiltrated into the surface layer of the bowling ball.

The application amount of the plasticizer is not particularly limited, and may be any amount that can wet the entire surface of the bowling ball. The application amount is preferably 1 to 50 ml, and the lower limit is preferably 2 ml or more, more preferably 3 ml or more, and still more preferably 4 ml or more. The upper limit is preferably 25 ml or less, more preferably 10 ml or less, and still more preferably 8 ml or less. By setting the application amount of the plasticizer in the above range, it is possible to efficiently apply the plasticizer to the entire surface of the bowling ball.

The temperature at which the plasticizer is applied in Step 2 is not particularly limited, but is preferably 0° C. or more and 150° C. or less. The lower limit value of the temperature at the time of application is preferably 20° C. or more, more preferably 40° C. or more, more preferably 50° C. or more, and particularly preferably 60° C. or more. The upper limit value is preferably 140° C. or less, more preferably 120° C. or less, more preferably 100° C. or less, and particularly preferably 80° C. or less. By setting the temperature at which the plasticizer is applied within the above range, the plasticizer can be efficiently infiltrated into the surface layer of the bowling ball.

As step 3, it is preferable to seal the bowling ball to which the plasticizer has been applied. As a sealing method, for example, it is preferable to seal with a plastic bag of polyethylene, polypropylene, or the like, a transparent film, or the like. After sealing, the bowling ball may be allowed to stand, or the sealed bowling ball may be flipped several times against a resilient member such as silicone. Alternatively, the sealed bowling ball may be pressurized using a pressurizing device or the like. The plasticizer can be efficiently infiltrated into the surface layer of the bowling ball. By sealing the bowling ball to which the plasticizer is applied, the plasticizer can be efficiently infiltrated into the surface layer of the bowling ball.

As Step 4, it is preferable that the bowling ball to which the plasticizer has been applied is kept for a predetermined time while the temperature of the bowling ball is adjusted. The temperature to be adjusted is preferably 150° C. or less. The lower limit value of the temperature to be adjusted is preferably 40° C. or more, more preferably 50° C. or more, more preferably 60° C. or more, and particularly preferably 70° C. or more. The upper limit value is preferably 140° C. or less, more preferably 120° C. or less, more preferably 100° C. or less, and particularly preferably 80° C. or less. Further, the temperature may be maintained at a constant temperature for the following retention time, or may be maintained while increasing or decreasing the temperature. In addition, the temperature may be changed over time, for example, from a high temperature to a low temperature and then returned to a high temperature, or from a low temperature to a high temperature and then returned to a low temperature.

Further, the holding time is not particularly limited, but is preferably 10 seconds or more and 72 hours or less. The lower limit of the holding time is preferably 1 minute or more, more preferably 1 hour or more, and still more preferably 12 hours or more. The upper limit is preferably 36 hours or less, more preferably 24 hours or less. By setting the heating time in the above range, the plasticizer composition can be efficiently infiltrated into the surface layer of the article. Note that the temperature does not necessarily need to be adjusted and maintained, and may be maintained at a temperature at the time of application, or may be naturally lowered to room temperature after application.

In the case where step 4 is not performed, it is preferable to provide a time for allowing the plasticizer to permeate the bowling ball after the plasticizer is applied. The time is not particularly limited, but is preferably 10 seconds or more and 72 hours or less. The lower limit of the permeation time is preferably 1 minute or more, more preferably 1 hour or more, and still more preferably 12 hours or more. The upper limit is preferably 36 hours or less, more preferably 24 hours or less. By setting the penetration time in the above range, the plasticizer can be efficiently penetrated into the surface layer of the bowling ball.

EXAMPLES

Hereinafter, the present invention will be described in more detail on the basis of examples, but the present invention is not limited to these examples. The plasticizers and bowling balls used in the examples are as follows:

<Adjustment of Plasticizer>
(A): JP120 benzoate (J-PLUS Co., Ltd.)
(B): 2-Ethylhexyl phthalate DOP (J-PLUS Co., Ltd.)

(A) 90 g of component (B) was weighed out, 10 g of component was added to the vessel and mixed at room temperature (25° C.) using a commercial mixer. No separation of the mixture was observed after 24 hours at 25° C.
<Bowling-Ball>

A bowling ball (serial number: 6G280539C) made of polyurethane as a surface layer resin and subjected to an oil extraction treatment was used.
<Maintenance Method of Bowling Ball>

Figure 1:
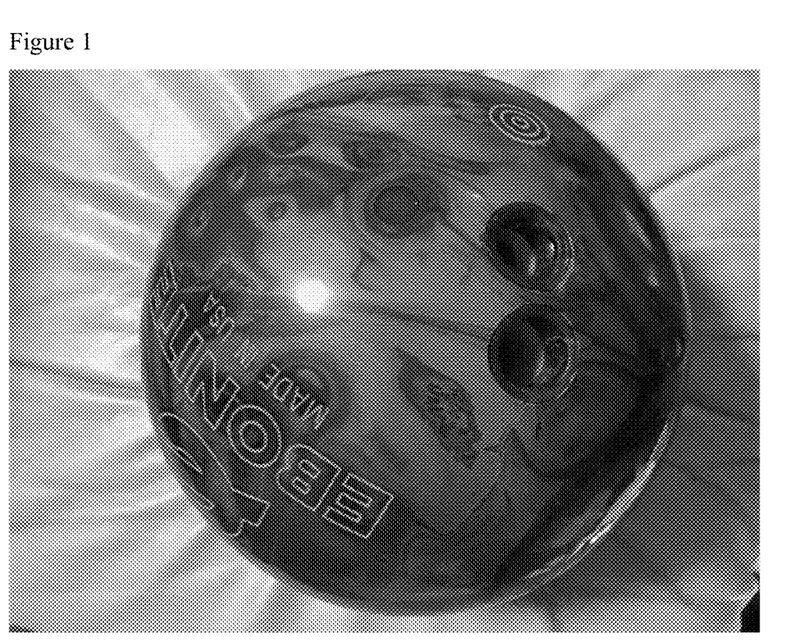
FIG. 1 shows an image of the bowling ball prior to application of the plasticizer.
Figure 2:
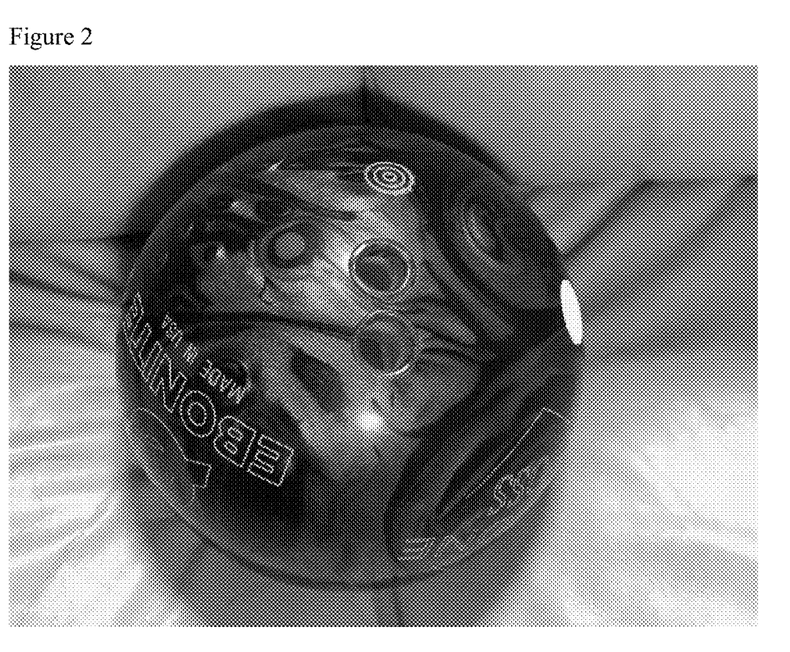
FIG. 2 shows an image of the bowling ball after application of the plasticizer.

As a maintenance method of bowling ball, the plasticizer prepared as described above was directly applied to the surface of the bowling ball subjected to the oil removal treatment under the condition of 60° C. After applying, the solution was left to reach room temperature (25° C.), sealed with a transparent film, and allowed to stand overnight (12 hours). Immediately after the application of the plasticizer, the surface of the bowling ball was sticky by the plasticizer, but after standing overnight, the stickiness of the surface was eliminated, and it was found that the plasticizer penetrated the surface resin of the bowling ball. The bowling ball prior to application of the plasticizer of the present invention is shown in FIG. 1 and the bowling ball prior to application is shown in FIG. 2. As a reference plasticizer, adipic polyester (D620N: J-PLUS Co., Ltd.) was used, and the same operations as described above were performed, and it was confirmed that the plasticizer was absorbed from the surfaces of the bowling balls.

The change in hardness of the bowling ball before and after application of the plasticizer, the feel of the surface, and the visual evaluation of the surface condition were carried out. The results are shown in Tables 1 and 2. The hardness of the bowling ball was measured by a durometer D (REX DUROMETER, TYPE D, Model:1700, manufactured by REX GAUGE Corporation) in an environment of 25 degrees Celsius, and the hardness of the unused ball is shown as a reference.
<Measurement Result of Hardness of Bowling Ball>

TABLE 1

| | Unused products | Before application of the plasticizer composition | After application of the plasticizer composition |
|---|---|---|---|
| Hardness (degrees) | 73 | 75 | 73 |

From the results in Table 1, it was found that the bowling ball to which the plasticizer of the present invention was applied had a reduced hardness and had a hardness equivalent to that of an unused product. This means that the plasticizer penetrates the resin of the surface layer of the bowling ball, thereby recovering the flexibility of the surface layer.
<Evaluation of Surface Condition by Visual Inspection and Feel of Bowling Ball Surface>

TABLE 2

| | Surface feel | Surface condition (visual) |
|---|---|---|
| Before application of the plasticizer composition | No gripping feeling on the surface | Non Glossy surface Whitish discoloration |

TABLE 2-continued

| | Surface feel | Surface condition (visual) |
|---|---|---|
| After application of the plasticizer composition | gripping feeling on the surface Same level of gripping feeling as unused products | Glossy surface Clear coloration Color similar to that of unused products |

From the results of Table 2, it was found that the surface layer of the bowling ball can be recovered by the penetration of the plasticizer into the surface layer of the bowling ball by the maintenance method of the present invention.

Further, in the above examples, the component (B) was changed to the component (C) described below, and the change in hardness of the bowling ball before and after the application of the plasticizer, the feel of the surface, and the visual evaluation of the surface state were performed.
(C): Tributyl Acetyl Citrate ATBC (J-PLUS Co., Ltd.)

It was confirmed that the same results as those described in the above Tables 1 and 2 were obtained by using tributyl acetyl citrate as the component (C) in place of bis(2-ethylhexyl) phthalate as the component (B). Next, in addition to 90 g of the component (A), the components (B) and (C) were evaluated in the same manner by using each of the components (B) and (C) in 5 g, and the same results as described above were obtained.

In addition, in the above examples, the same evaluations were carried out using the compositions containing bis(2-ethylhexyl) phthalate as the component (B) and tributyl acetyl citrate as the component (C), or the components (A) to (C) alone without containing the benzoic acid glycol ester JP120 as the component (A), but the same results as described above were obtained with respect to the hardness of the bowling ball.

INDUSTRIAL APPLICABILITY

The maintenance method of the bowling ball of the present invention is to apply a plasticizer to the bowling ball in which the plasticizer volatilizes or elutes and the flexibility of the surface layer is lost, thereby allowing the plasticizer to penetrate the surface layer and recover the flexibility of the surface layer of the bowling ball.

The preceding description is merely to illustrate and describe exemplary embodiments of the claimed invention. It is not intended to be exhaustive or limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, the invention is not limited to the particular embodiment disclosed as the best mode contemplated for carrying out this invention, but the invention includes all embodiments falling within the scope of the claims. The invention may be practiced otherwise than is specifically explained and illustrated without departing from its spirit or scope.

What is claimed is:

1. A bowling ball treatment method comprising, the following steps of:
  preparing a bowling ball; and
  applying a plasticizer is applied to an outer peripheral surface layer of the bowling ball prepared in the step of preparing the bowling ball, without forming a resin layer on the outer peripheral surface layer.

2. The bowling ball treatment method according to claim 1, wherein the plasticizer is a compound having an oxyalkylene group.

3. The bowling ball treatment method according to claim 1, wherein the plasticizer is one or more compounds represented by the general formula (1):

in the above formula, $R^1$ independently represents a hydrocarbon group having 1 to 10 carbon atoms, and $R^2$ independently represents a hydrocarbon group having 1 to 30 carbon atoms or a halogen atom, wherein the hydrocarbon group may contain a heteroatom, wherein n is a repeat number, represents an integer of 1 or more, and p represents an integer of 0 to 5, respectively.

4. The bowling ball treatment method according to claim 1, wherein the plasticizer is (B) one or more of the compounds represented by the general formula (2):

in the above formula, $R^3$ represents a hydrocarbon group having 1 to 20 carbon atoms, wherein the hydrocarbon group may contain a heteroatom, $R^4$ independently represents a hydrocarbon group having 1 to 30 carbon atoms or a halogen atom, wherein the hydrocarbon group may contain a heteroatom, and m represents an integer of 0 to 5.

5. The bowling ball treatment method according to claim 1, wherein the plasticizer is one or more compounds represented by the general formula (3):

in the above formula, $R^5$, $R^6$ independently represents a hydrogen atom or a hydrocarbon group having 1 to 20 carbon atoms, wherein the hydrocarbon group may contain a heteroatom.

6. The bowling ball treatment method according to claim 1, wherein the outer peripheral surface layer of the bowling ball is one or more resins selected from ebonite, polyester, polyethylene, polypropylene, polycarbonate, polyamide, polyurethane, polyimide, acrylic resin, polylactic acid, polyvinyl chloride, polybutadiene, polyisoprene, and epoxy resin.

7. The bowling ball treatment method according to claim 1, wherein the bowling ball is subjected to an oil removal treatment.

8. The bowling ball treatment method according to claim 1, further comprising any or both of the following steps sealing the bowling ball applied with the plasticizer the step of applying plasticizer; and holding the bowling ball for a fixed time while adjusting the temperature of the bowling.

* * * * *